United States Patent
Musikant (10) Patent No.: US 10,561,475 B2
(45) Date of Patent: Feb. 18, 2020

(54) NON-CIRCULAR ENDODONTIC INSTRUMENTS

(71) Applicant: Essential Dental Systems, Inc., South Hackensack, NJ (US)

(72) Inventor: Barry L. Musikant, New York, NY (US)

(73) Assignee: Essential Dental Systems, Inc., South Hackensack, NJ (US)

( * ) Notice: Subject to any disclaimer, the term of this patent is extended or adjusted under 35 U.S.C. 154(b) by 32 days.

(21) Appl. No.: 15/408,608

(22) Filed: Jan. 18, 2017

(65) Prior Publication Data

US 2017/0265964 A1 Sep. 21, 2017

Related U.S. Application Data (60) Provisional application No. 62/308,622, filed on Mar. 15, 2016.

(51) Int. Cl.
*A61C 5/42* (2017.01)
*A61C 19/02* (2006.01)

(52) U.S. Cl.
CPC ............ *A61C 5/42* (2017.02); *A61C 19/02* (2013.01)

(58) Field of Classification Search
CPC .... A61C 5/42; A61C 5/40; A61C 3/02; B23B 51/02; B23B 2251/40; B23B 2251/46; B23B 2251/48; B23B 2270/30
See application file for complete search history.

(56) References Cited

U.S. PATENT DOCUMENTS

| 444,383 A | 1/1891 | Ivory |
| 1,067,015 A | 7/1913 | Fowler |
| 1,527,845 A | 2/1925 | Daniel |
| 4,260,379 A | 4/1981 | Groves et al. |
| 4,285,618 A * | 8/1981 | Shanley, Jr. ............ B23C 5/10 |
| | | 407/54 |

(Continued)

FOREIGN PATENT DOCUMENTS

| EP | 1108396 A2 | 6/2001 |
| EP | 1716818 A1 | 11/2006 |

(Continued)

OTHER PUBLICATIONS

International Search Report for Application No. PCT/US2017/020097, dated Jun. 7, 2017.

(Continued)

*Primary Examiner* — Edward Moran
(74) *Attorney, Agent, or Firm* — Lerner, David, Littenberg, Krumholz & Mentlik, LLP

(57) ABSTRACT

An endodontic instrument includes a cutting portion having upper and lower ends spaced apart along an axis, a cutting surface extending helically along the axis, and a non-contact surface extending helically along the axis. A cross section of the cutting portion in a plane perpendicular to the axis has a non-circular circumference. The cutting surface extends about a first portion of the non-circular circumference, and the non-contact surface forms a linear segment that extends about a second portion of the non-circular circumference. The cutting portion can further include a second cutting surface extending helically along the axis, and a second non-contact surface extending helically along the axis.

14 Claims, 9 Drawing Sheets

(56) References Cited

U.S. PATENT DOCUMENTS

| | | | |
|---|---|---|---|
| 4,395,167 A * | 7/1983 | Maternus | B23B 51/08 407/54 |
| 4,634,378 A | 1/1987 | Leonard | |
| 4,661,061 A | 4/1987 | Martin | |
| 4,836,780 A | 6/1989 | Buchanan | |
| 4,934,934 A | 6/1990 | Arpaio, Jr. et al. | |
| 4,990,088 A | 2/1991 | Weissman | |
| 5,426,988 A | 6/1995 | Ohata et al. | |
| 5,464,362 A | 11/1995 | Heath et al. | |
| 5,762,497 A | 6/1998 | Heath | |
| 6,042,376 A | 3/2000 | Cohen et al. | |
| 6,712,611 B2 * | 3/2004 | Garman | B24B 19/022 433/102 |
| 7,311,522 B2 * | 12/2007 | Graybill | B23H 5/06 433/102 |
| 7,621,699 B2 * | 11/2009 | McAuliffe | B24D 7/18 407/53 |
| 8,454,361 B2 * | 6/2013 | Scianamblo | A61C 5/42 433/102 |
| 2003/0211442 A1 | 11/2003 | Abel | |
| 2005/0272004 A1 * | 12/2005 | Desrosiers | A61C 8/0089 433/102 |
| 2008/0023720 A1 | 1/2008 | Yang et al. | |
| 2008/0176191 A1 * | 7/2008 | Koch | A61C 5/42 433/224 |
| 2012/0009543 A1 * | 1/2012 | Meier | A61B 17/1615 433/165 |
| 2012/0094252 A1 | 4/2012 | Johnson | |
| 2012/0208146 A1 | 8/2012 | Mordeniz | |

FOREIGN PATENT DOCUMENTS

| | | |
|---|---|---|
| EP | 1749498 A1 | 2/2007 |
| WO | 9721392 A1 | 6/1997 |

OTHER PUBLICATIONS

Supplementary European Search Report for EP17767155 dated Jan. 25, 2019.

* cited by examiner

FIGURE 1

Prior art

| DESIGN | MAX STRESS | FACTOR OF SAFETY | FATIGUE RESULTS |
|---|---|---|---|
| First Conventional Design | 189,812,000 N/m^2 | 1.08 | 374,455 cycles |
| Second Conventional Design | 225,368,000 N/m^2 | 0.90 | 171,425 cycles |
| Novel Design | 189,882,000 N/m^2 | 1.07 | 373,885 cycles |

FIGURE 8

| DESIGN | MAX STRESS | DISPLACEMENT |
|---|---|---|
| First Conventional Design | 5.35836e+009 N/m^2 | 21.4931 mm MAX |
| Second Conventional Design | 1.59863e+010 N/m^2 | 29.3185 mm MAX |
| Novel Design | 7.62838e+009 N/m^2 | 22.5165 mm MAX |

FIGURE 9

NON-CIRCULAR ENDODONTIC INSTRUMENTS

CROSS-REFERENCE TO RELATED APPLICATIONS

This application claims the benefit of the filing date of U.S. Provisional Patent Application No. 62/308,622 filed Mar. 15, 2016, the disclosure of which is hereby incorporated herein by reference.

BACKGROUND OF THE INVENTION

This invention relates to endodontic instruments having non-circular cross sections, and more specifically, to endodontic instruments for removing pulp tissue and widening root canals that include helical cutting surfaces and helical non-contact surfaces for improving performance, decreasing stress, and removing debris during operation.

When a diseased root canal (diseased pulp tissue) is found in the root canal of a patient's tooth, a dentist removes the pulp tissue in order to get access to the most apical end of the tooth where bacteria is normally found. Usually a series of files or reamers (hand instruments or rotary instruments) which have a circular cross section are used to both remove the pulp tissue and to widen the root canal. Along with the tissue being removed mechanically, irrigation solutions like sodium hypochlorite (NaOCl) are used to kill any remaining bacteria and digest tissue remnants. Then the root canal is filled with gutta-percha and adhesive and sealed-off with such root canal preparations as the one sold by Essential Dental Systems, Inc. under the trademark EZ-Fill. Lastly, a crown could be fitted to the tooth.

The traditional endodontic instrument used to remove pulp tissue or dentin in the root canal has a circular cross section. As the instrument engages the dentin, it creates a contact surface extending 360 degrees about the narrowest part of the canal. This complete circumferential contact creates resistance to the rotation of the instrument as it removes dentin. The resistance is transferred to both the instrument and the tooth in the form of stress. The greater the resistance, the greater the stress. Because the tooth is much thicker than the reamer or file, it has a minimal chance of distorting or fracturing. The reamer or file, which can be hand or rotary driven however, can easily distort by unwinding when engagement along the shank produces excessive torque generated by either hand or motor powered rotation. In fact, if rotation with excessive torque continues, the stainless steel reamer can unwind and then fracture. Ni—Ti (Nickel-titanium) instrumentation will generally fracture much more abruptly given the same amount of torque because the Ni—Ti alloy is more flexible with a much lower elastic limit.

One way to reduce the chances of excessive engagement is by using a sequence of ever thickening instruments that remove the dentin in a gradual fashion. In theory, each succeeding reamer or file widens the canal enough to allow the incremental removal of dentin with the subsequent reamer or file never creating sufficient engagement for distortion during rotation. This technique is known as stepback because the wider reamers or files are also taken to a shallower depth to further minimize stress and distortion to the instrument.

Another technique employed in endodontics is called crown-down. It employs wider instruments first to open up the coronal aspects of the canal, and subsequently thinner reamers and files are placed more and more apically. Both techniques attempt to reduce the amount of torque generated by limiting the degree of dentin engagement that the reamers and files encounter, to prevent excessive engagement of dentin which leads to distortion and potential fracture of the instruments.

Figure 1:
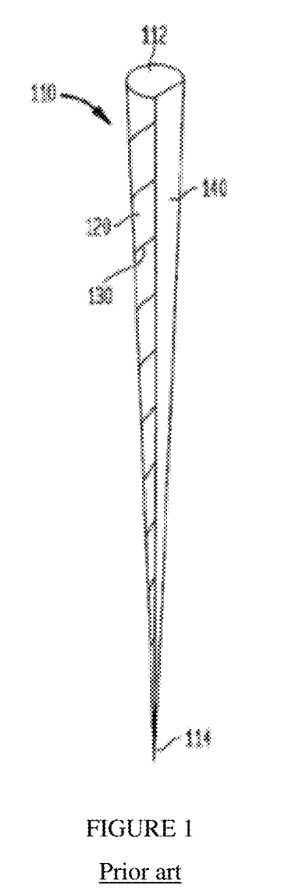
FIG. 1 is a perspective view of a prior art endodontic instrument having a cutting surface and a non-contact area linearly extending along the length of the instrument.

The implementation of these techniques with an endodontic instrument which does not make full engagement with the dentin in a root canal as taught, for example, in U.S. Pat. No. 6,042,376 entitled "Non-circular endodontic instruments" to Cohen, et al. ("the '376 Patent"), have resulted in the reduction of stress and the facilitation of debris removal from the root canal during endodontic instrumentation. FIG. 1 shows an embodiment of the '376 Patent in which an endodontic instrument 110 has an upper end 112 tapering along its length to a lower end 114, a cutting surface 120 including cutting blades 130 extending helically along cutting surface 120, and a non-contact area 140. Cutting surface 120 extends along the length of instrument 110 about a portion of the circumference of instrument 110. Non-contact area 140 also extends along the length of instrument 110 about a portion of the circumference of instrument 110.

In use, when the instrument of the '376 Patent is inserted into a canal and rotated, the cutting surface with the cutting blades engages the canal and removes dentin therefrom. The non-contact area does not engage the canal and thus reduces the stress that would be caused by the engagement of a completely circumferential cutting face with the canal. The non-contact area also provides an area for debris to gather and be maintained out of the way of the cutting face. However, when the instrument is used in reciprocation, there is a portion of the canal wall that remains unengaged, compromising the effectiveness of the canal cleansing.

There is a need for stronger endodontic instruments having improved configurations to resist fracturing and that also improve facilitation of debris removal from the root canal.

BRIEF SUMMARY OF THE INVENTION

A first aspect of the present invention is an endodontic instrument including a cutting portion having upper and lower ends spaced apart along an axis, a cutting surface extending helically along the axis, and a non-contact surface extending helically along the axis, wherein a cross section of the cutting portion in a plane perpendicular to the axis has a non-circular circumference, and wherein the cutting surface extends about a first portion of the non-circular circumference, and the non-contact surface forms a linear segment that extends about a second portion of the non-circular circumference.

In accordance with other embodiments of the first aspect, every cross section of the cutting portion along the axis in a plane perpendicular to the axis may have a non-circular circumference. The lower end of the cutting portion may be a pointed lower end or a rounded lower end. The pointed lower end may have a cutting tip or a non-cutting tip. The non-contact surface may be uninterrupted along the cutting portion or may be interrupted along the cutting portion into two or more segments. The cutting portion may have a length defined along the axis between the upper and lower ends. The first portion of the circumference about which the cutting surface extends may be generally circular.

The cutting surface may include cutting blades. The cutting blades may extend helically along the cutting surface. The cutting surface may extend helically along the axis in a first direction, and the cutting blades may extend helically along the cutting surface in a second direction opposite from the first direction. The first direction may be a left handed helical twist and the second direction may be a right handed helical twist. The cutting surface may extend helically along the axis in a first direction, and the cutting blades may extend helically along the cutting surface in the first direction. The cutting portion may taper from the upper end to the lower end. The non-contact surface may have a taper corresponding to a taper of the cutting portion. The non-contact surface may extend helically to the axis of the cutting portion.

The cutting portion may further include a second cutting surface extending helically along the axis, and a second non-contact surface extending helically along the axis, wherein the non-circular circumference includes a third portion about which the second cutting surface extends and a fourth portion about which the second non-contact surface extends and forms a second linear segment of the circumference. The third portion of the circumference about which the second cutting surface extends may be generally circular. The first and third generally circular portions of the circumference may oppose one another. The second and fourth portions having the first and second linear segments, respectively, may be positioned between the first and third generally circular portions of the circumference. The second cutting surface may include cutting blades. The cutting blades of the second cutting surface may extend helically along the second cutting surface. The second non-contact surface may extend helically to the axis of the cutting portion.

The cutting portion may be comprised of metal. The cutting portion may be made from one of stainless steel, nickel titanium, inconel, ceramic, carbide, metal alloys of iron, nickel, titanium, tungsten, copper, niobium, hafnium, aluminum, brass, bronze, galvanized steel, high carbon steel, and alloys and combinations thereof. The cutting portion may be comprised of plastic.

The ratio of a length of the first portion of the non-circular circumference to a length of the second portion of the non-circular circumference may be about 1:1, 2:1, or 4:1. A length of the cutting portion may be between 5 and 80 mm. A diameter of the cutting portion may be between 0.02 and 8.0 mm. The cutting portion may taper from the upper end to the lower end so that a diameter of the upper end is between 0.02 and 1.0 mm greater than a diameter of the lower end.

A second aspect of the present invention is a kit including two or more endodontic instruments each having a different size or shape. Each endodontic instrument includes a cutting portion having upper and lower ends spaced apart along an axis, a cutting surface extending helically along the axis, and a non-contact surface extending helically along the axis, wherein a cross section of the cutting portion in a plane perpendicular to the axis has a non-circular circumference, and wherein the cutting surface extends about a first portion of the non-circular circumference, and the non-contact surface forms a linear segment that extends about a second portion of the non-circular circumference.

A third aspect of the present invention is a method of using the endodontic instrument. The endodontic instrument includes a cutting portion having upper and lower ends spaced apart along an axis, a cutting surface extending helically along the axis, and a non-contact surface extending helically along the axis, wherein a cross section of the cutting portion in a plane perpendicular to the axis has a non-circular circumference, and wherein the cutting surface extends about a first portion of the non-circular circumference, and the non-contact surface forms a linear segment that extends about a second portion of the non-circular circumference. The method includes the steps of inserting the cutting portion of the instrument at least partially into a root canal, and reciprocating the instrument along the axis of the cutting portion to remove dentin.

In accordance with other embodiments of the third aspect, the method may further include rotating the instrument about the axis of the cutting portion. The step of reciprocating may include using a powered device to operate the instrument. The step of reciprocating may include manually operating the instrument.

A fourth aspect of the present invention is an endodontic instrument including a cutting portion having upper and lower ends spaced apart along an axis, a cutting surface extending helically along the axis, and a non-contact surface extending helically along the axis, wherein a cross section of the cutting portion in a plane perpendicular to the axis has a non-circular perimeter, and wherein the cutting surface extends about an arc-shaped first portion of the non-circular perimeter, and the non-contact surface extends about a linear second portion of the non-circular circumference.

In accordance with other embodiments of the fourth aspect, the arc-shaped first portion of the non-circular circumference may be connected at each end thereof with respective ends of the linear second portion of the non-circular circumference.

A fifth aspect of the present invention is an endodontic instrument including a cutting portion having upper and lower ends spaced apart along an axis, first and second cutting surfaces extending helically along the axis, and first and second non-contact surfaces extending helically along the axis, wherein a cross section of the cutting portion in a plane perpendicular to the axis has a non-circular circumference, and wherein the first cutting surface extends about a first generally circular portion of the non-circular circumference, the first non-contact surface forms a linear segment that extends about a second portion of the non-circular circumference, the second cutting surface extends about a third generally circular portion of the non-circular circumference, and the second non-contact surface forms a linear segment that extends about a fourth portion of the non-circular circumference.

In accordance with other embodiments of the fifth aspect, the first and second cutting surfaces may each include cutting blades. The first and third generally circular portions of the circumference may oppose one another. The second and fourth portions having the first and second linear segments, respectively, may be positioned between the first and third generally circular portions of the circumference.

A sixth aspect of the present invention is an endodontic instrument including a cutting portion having upper and lower ends spaced apart along an axis, first and second cutting surfaces extending helically along the axis, and first and second non-contact surfaces extending helically along the axis, wherein a cross section of the cutting portion in a plane perpendicular to the axis has a non-circular perimeter, and wherein the first cutting surface extends about an arc-shaped first portion of the non-circular perimeter, the first non-contact surface extends about a linear second portion of the non-circular perimeter, the second cutting surface extends about an arc-shaped third portion of the non-circular perimeter, and the second non-contact surface extends about a linear fourth portion of the non-circular circumference.

In accordance with other embodiments of the sixth aspect, the arc-shaped first portion of the non-circular circumference may be connected at each end thereof with an end of the linear second portion and an end of the linear fourth portion, respectively, and wherein the arc-shaped third portion of the non-circular circumference is connected at each end thereof with another end of the linear second portion and another end of the linear fourth portion, respectively.

A seventh aspect of the present invention is a method of making an endodontic instrument including obtaining a substrate having upper and lower ends spaced apart along an axis and an outer surface that tapers from the upper end to the lower end, wherein a cross section of the substrate in a plane perpendicular to the axis has a perimeter defined by a plurality of linear segments and corners formed between adjacent segments, twisting one of the upper and lower ends with respect to the other to form a cutting surface along a cutting portion of the substrate, such that the cutting surface extends about the entirety of a circumference of the substrate in a cross section of the cutting portion in a plane perpendicular to the axis, and removing material from the substrate in a helical path along the axis to form a non-contact surface, such that the cutting surface also extends helically along the axis, and such that the circumference of a cross section of the cutting portion is non-circular.

In accordance with other embodiments of the seventh aspect, the step of obtaining may include manufacturing or acquiring the substrate. The step of obtaining may include the substrate having substantially axial cutting blades extending generally parallel to the axis and defined by the corners of the perimeter. The step of twisting may transform the substantially axial cutting blades into helical cutting blades. The step of removing may result in the helical path extending along the axis in a first direction, and the step of twisting may result in the helical cutting blades each extending along the cutting surface in a second direction opposite from the first direction.

The step of twisting may include twisting the one of the upper and lower ends between five and thirty revolutions about the axis. The step of twisting may include twisting the one of the upper and lower ends sixteen revolutions about the axis. The step of removing may include grinding or milling the material from the substrate. The step of removing may include removing the material at least to a minimum diameter of the cutting surface. The step of removing may include forming a linear segment of the non-circular circumference that defines the non-contact surface. The cutting surface may extend about a first portion of the non-circular circumference, and the non-contact surface may form a linear segment that extends about a second portion of the non-circular circumference. The perimeter may be square shaped or triangular.

An eighth aspect of the present invention is a method of making an endodontic instrument including obtaining a substrate having upper and lower ends spaced apart along an axis and an outer surface that tapers from the upper end to the lower end, wherein a cross section of the substrate in a plane perpendicular to the axis has a perimeter defined by a plurality of linear segments and corners formed between adjacent segments, removing material from the substrate in a helical path along the axis to form a non-contact surface, the non-contact surface being adjacent to an undisturbed surface of the substrate, and twisting one of the upper and lower ends with respect to the other to form the undisturbed surface into a cutting surface along a cutting portion of the substrate, such that the cutting surface and the non-contact surface both extend helically along the axis, and such that the circumference of a cross section of the cutting portion is non-circular.

In accordance with other embodiments of the seventh aspect, the step of obtaining may include manufacturing or acquiring the substrate. The step of obtaining may include the substrate having substantially axial cutting blades extending generally parallel to the axis and defined by the corners of the perimeter. The step of twisting may transform the substantially axial cutting blades into helical cutting blades. The step of removing may result in the helical path extending along the axis in a first direction, and the step of twisting may result in the helical cutting blades each extending along the cutting surface in a second direction opposite from the first direction.

The step of twisting may include twisting the one of the upper and lower ends between five and thirty revolutions about the axis. The step of twisting may include twisting the one of the upper and lower ends sixteen revolutions about the axis. The step of removing may include grinding or milling the material from the substrate. The step of removing may include removing the material at least to a minimum diameter of the substrate. The step of removing may include forming a linear segment of the non-circular circumference that defines the non-contact surface. The cutting surface may extend about a first portion of the non-circular circumference, and the non-contact surface may form a linear segment that extends about a second portion of the non-circular circumference. The perimeter may be square shaped or triangular.

DETAILED DESCRIPTION

An endodontic instrument 200 according to one embodiment of the present invention is shown in FIGS. 2A, 2B, 3A-3C, and 4. Instrument 200 has a body with a cutting portion that tapers down from an upper end 202 to a pointed lower end 204. Pointed lower end 204 can have a cutting tip or a non-cutting tip. In other embodiments, lower end 204 can be rounded. Upper and lower ends 202, 204 are spaced apart along a central axis of the body such that the cutting portion has a length defined along the axis between upper and lower ends 202, 204. Along the cutting portion of the body, instrument 200 has a cross section in a plane perpendicular to the axis of the body that has a non-circular circumference, which is shown more clearly in FIGS. 3B and 3C.

The cutting portion includes a cutting surface 206 extending helically along the cutting length of instrument 200. Cutting blades 208 extend helically along cutting surface 206 and from an inner diameter 212 to an outer diameter 214, as shown in FIGS. 3B and 3C. Cutting surface 206 extends about a first portion of the non-circular circumference of the cutting portion. Cutting surface 206 extends helically along the axis of instrument 200 in a first direction, shown in FIGS. 2A and 2B as a "left handed" helical twist, while cutting blades 208 extend helically along instrument 200 in an opposite second direction, shown in FIGS. 2A and 2B as a "right handed" helical twist. In other embodiments, cutting blades can extend helically along the instrument in the same first direction as the cutting surface.

Figure 4:
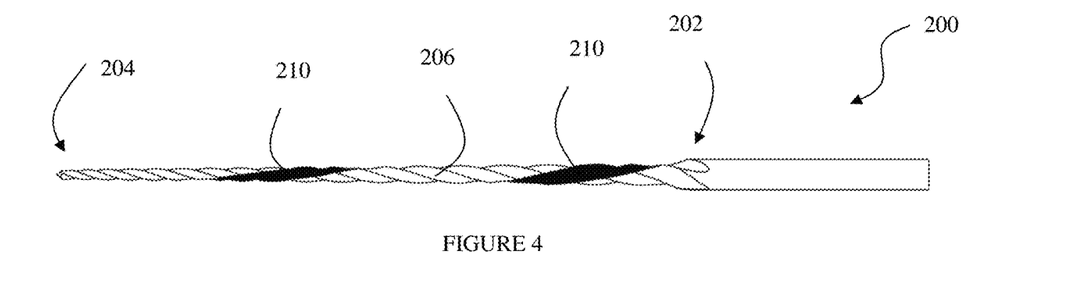
FIG. 4 is another plan view of the instrument shown in FIGS. 2A and 2B.

The cutting surface further includes a non-contact surface 210 extending helically in the first direction along the length of instrument 200. Non-contact surface 210 forms a linear segment that extends about a second portion of the non-circular circumference and is tangential to inner diameter 212 of cutting blades 208. Non-contact surface 210 is uninterrupted along the length of the cutting portion in that it extends continuously from upper end 202 to lower end 204, as shown in FIG. 4. Non-contact surface 210 can have a taper corresponding to a taper of the cutting portion. Where the cutting portion extends all the way to pointed lower end 204, non-contact surface 210 can extend helically to the axis of the cutting portion, such that every cross section of the cutting portion along the axis in a plane perpendicular to the axis has a linear segment formed by the non-contact surface, such that the non-contact surface formed by the linear segments extends continuously and uninterrupted along the entire cutting portion. Together, cutting surface 206 and non-contact surface 210 make up the entire outer surface of instrument 200 to allow for the highly efficient shaping of the root canal while simultaneously removing debris.

Figure 5:
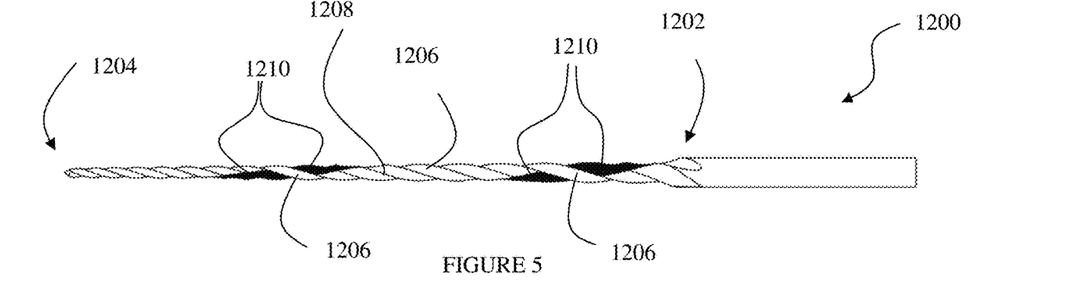
FIG. 5 is a plan view an endodontic instrument having a cutting surface and an interrupted non-contact surface helically extending along the length of the instrument according to another embodiment of the present invention.
Figure 6:
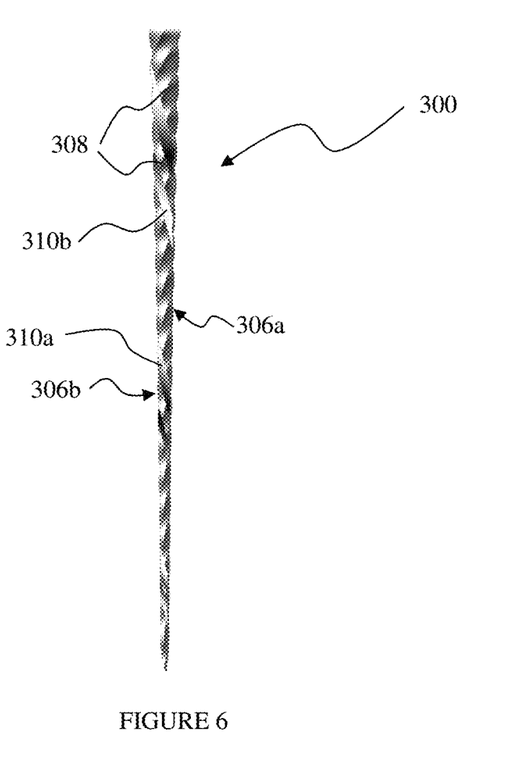
FIG. 6 is a perspective view of an endodontic instrument having two non-contact surfaces helically extending in parallel along the length of the instrument according to another embodiment of the present invention.

In other embodiments, the non-contact surface can be interrupted. For example, FIG. 5 shows an instrument 1200 similar in many respects to instrument 200. The cutting surface of instrument 1200 includes a non-contact surface 1210 extending helically in the first direction along the length of instrument 1200. Different from that of instrument 200, non-contact surface 1210 is interrupted along the length of the cutting portion in that it extends in segments from upper end 1202 to lower end 1204, as shown in FIG. 5. These segments can be separated by the space between adjacent cutting blades 1208 of cutting surface 1206.

The introduction of a helical array of cutting and non-cutting edges allows for the rapid shaping and cleaning of root canals while evenly disbursing torsional stresses ensuring far less breakage and instrument failure. The helical design of cutting surface 206 and non-contact surface 210 allows for 360 degrees of engagement of instrument 200 with the tooth when used by rotating or propagating instrument 200. In this way, every cross section of the cutting portion along the axis between upper and lower ends 202, 204 in a plane perpendicular to the axis has a non-circular circumference. The present endodontic instruments provide a reduction of stress during removal of dentin without compromising the cleansing of the root canal. The incorporation of a non-circular cross-section reduces stress and provides for a location for debris to collect away from cutting areas.

As indicated above, the non-circular cross-section may be comprised of one generally circular portion truncated by one flat area that is linear in cross-section. That is, the first portion of the non-circular circumference having cutting surface 206 is generally circular such that the non-circular circumference is D-shaped. The non-circular cross section, taken in a plane perpendicular to a length of the instrument, can be defined by a perimeter having an arc-shaped portion connected at each end to the ends of a linear portion. While cutting surface 206 extends around the circumference or perimeter of instrument 200 in a generally circular manner, the edge of instrument 200 is not arc shaped itself as shown in the cross sectional views of FIGS. 3B and 3C. The geometry of the edge is accounted for by the configuration of cutting blades 208 of cutting surface 206.

In a preferred embodiment, the endodontic instrument of the present invention provides for a cutting surface or face that is generally circular in cross-section or arc-shaped and extends about a portion of the circumference of the instrument, but is interrupted, at one circumferential location of the instrument, by a non-contact surface or face, which helically extends along the cutting length. The instrument can have more than one non-contact surface or area and/or more than one cutting surface, as described below.

A method of making an instrument described herein, such as instrument 200, involves first obtaining a substrate that has upper and lower ends spaced apart along its axis and an outer surface that tapers from the upper end to the lower end. A cross section of the substrate in a plane perpendicular to the axis has a perimeter defined by a plurality of linear segments and corners formed between adjacent segments. That is, the perimeter can be square shaped, triangular, or anther polygonal cross sectional shape. This type of perimeter can be seen in FIGS. 3B and 3C. The substrate is configured such that the cross sectional perimeter does not rotate along the axis. In other words, the substrate is shaped like a pyramid having substantially axial cutting blades extending generally parallel to its axis that are defined by the corners of the perimeter. Obtaining such a substrate can include manufacturing or otherwise acquiring the substrate, which is made of metal such as stainless steel, nickel titanium, or other materials as described herein.

The substrate is then heated and twisted so that the substantially axial cutting blades are transformed into helical cutting blades. This includes twisting one of the upper and lower ends with respect to the other to form a cutting surface along a cutting portion of the substrate. At this stage, the cutting surface extends about the entirety of a circumference of the substrate in a cross section of the cutting portion in a plane perpendicular to the axis. The substrate can be twisted so that one end completes sixteen revolutions about the axis. Other configurations are possible, such as those that twist between five and thirty revolutions about the axis.

At this point, material is removed from the substrate in a helical path along the axis to form a non-contact surface. That is, the location at which material is removed travels along a helical path such that the cutting surface also extends helically along the axis. The removal of material can include grinding, milling, or the like and can result in the non-contact surface being located at or beneath a minimum diameter of the cutting surface. This results in the circumference of a cross section of the cutting portion being non-circular. As indicated above, this creation of the non-contact surface can result in its helical path extending along the axis in a first direction, and while the helical cutting blades each extending along the cutting surface in a second direction opposite from the first direction.

In another method of making an instrument described herein, after the substrate described above is obtained, material can be removed from the substrate in a helical path along the axis to form the non-contact surface. As a result of the removal step being carried out earlier in the process, the non-contact surface is adjacent to an undisturbed surface of the substrate. Then the substrate can be twisted to form the undisturbed surface into a cutting surface along a cutting portion of the substrate such that the cutting surface and the non-contact surface both extend helically along the axis. The exact configuration of the initial helical path of the non-contact surface will be altered during this process, which can be accounted for during the step of removing material from the substrate. From here, other steps can be carried out as discussed above.

Figures 7A, 7B:
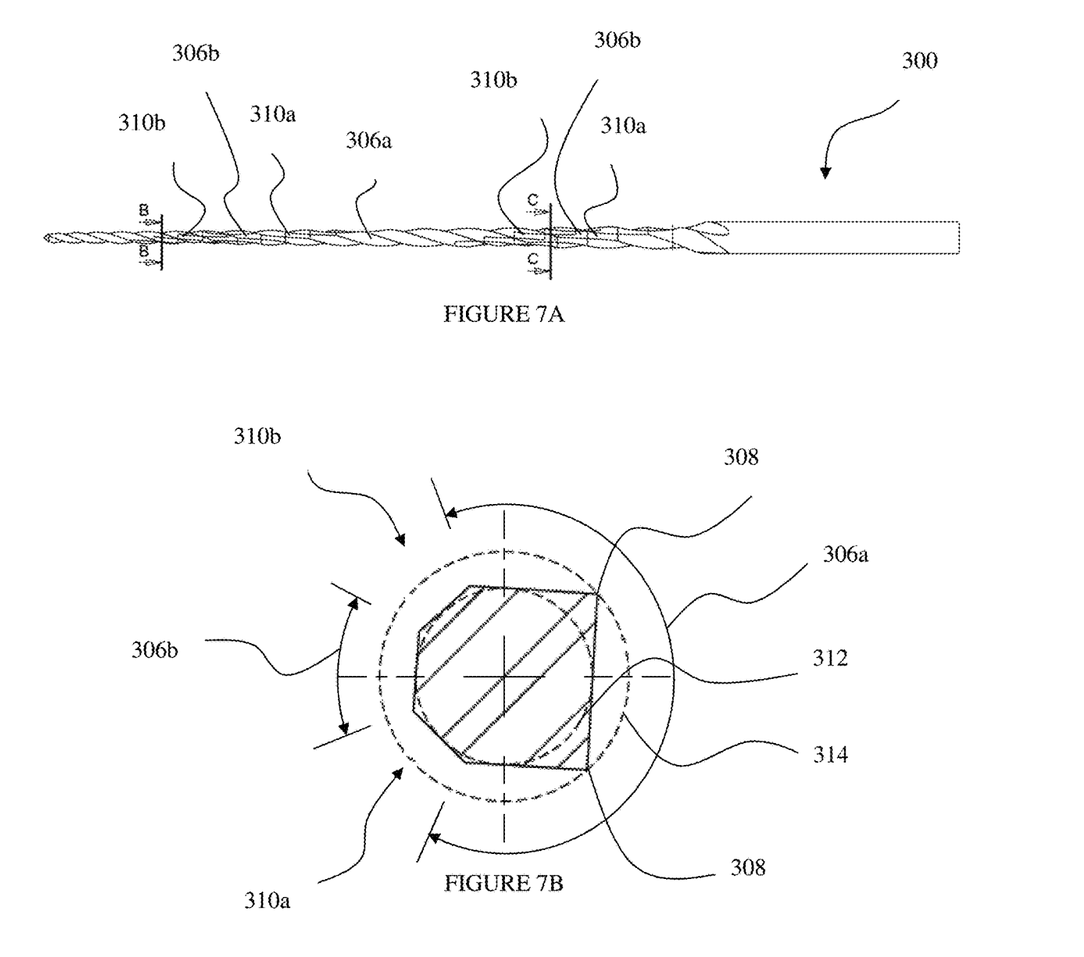
FIG. 7A is a plan view of the instrument shown in FIG. 6.
FIGS. 7B and 7C are sectional views taken along the lines B-B and C-C, respectively, of FIG. 7A.
Figure 7C:
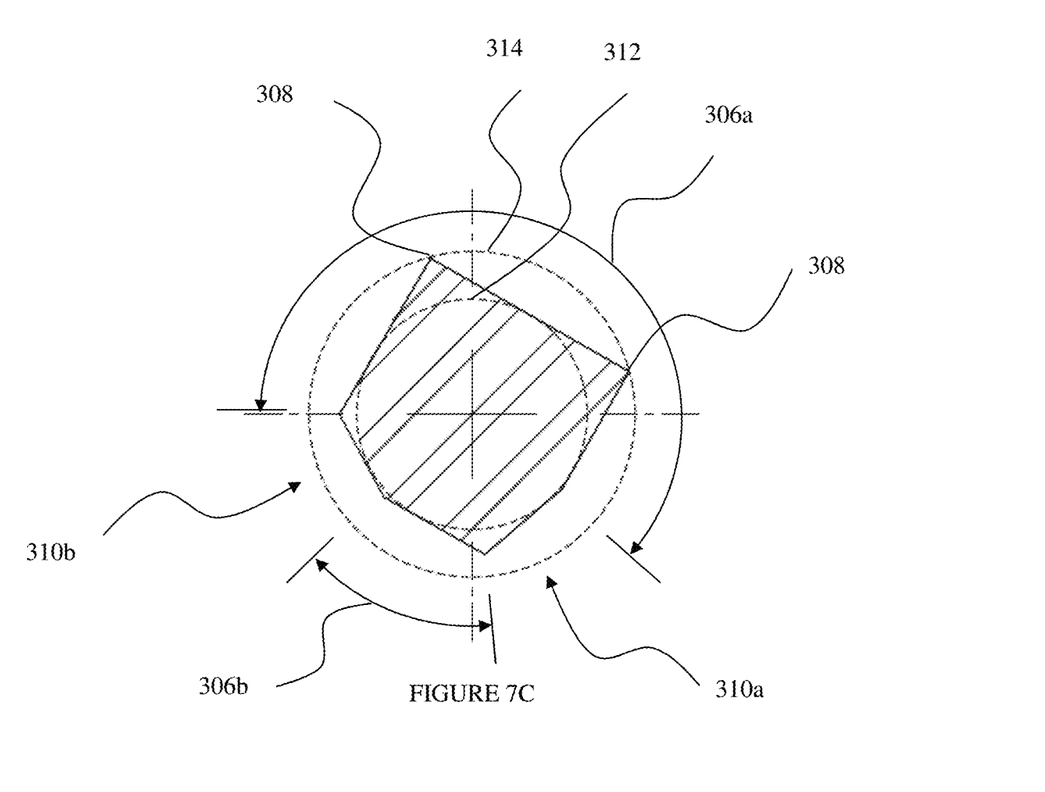

Another embodiment of an endodontic instrument 300 is shown in FIGS. 6 and 7A-C. Instrument 300 is similar in nature to instrument 200 but includes multiple non-contact surfaces helically extending along the cutting length at a smaller pitch. In between the non-contact surfaces are multiple cutting surfaces that also extend along the cutting length. Cutting surfaces 306a and 306b each include cutting blades 308 extending helically along the cutting length of instrument 300 and from an inner diameter 312 to an outer diameter 314, as shown in FIGS. 7B and 7C. Cutting surfaces 306a and 306b extend helically along the instrument in a first direction, while cutting blades 308 extend helically along the instrument in an opposite second direction. Cutting surfaces 306a and 306b extend about respective portions of the non-circular circumference of the cutting portion. Non-contact surfaces 310a and 310b extend helically in the first direction along the length of instrument 300, and can extend to the axis of the cutting portion. Non-contact surfaces 310a and 310b each form linear segments that extend about respective portions of the non-circular circumference.

That is, the non-circular cross-section of instrument 300 includes two generally circular portions separated by two linear portions. The non-circular cross section is therefore defined by a perimeter having first and second arc-shaped portions, shown more clearly in FIGS. 7B and 7C, that are connected through first and second linear portions. The two generally curved cutting faces are positioned in a circumferentially opposing relationship and along the length of the instrument, and two non-contact surfaces are positioned between the cutting faces. The two non-contact surfaces helically extend in parallel along the length of the instrument.

Importantly, the present invention provides for reduced stress to the tooth and to the cutting instrument during the removal of dentin from a root canal by providing at least one area of non-contact, i.e. one portion of the instrument does not contact and does not cut the dentin material, but is recessed back from the general circular cross-sectional shape of the device to reduce stress to the tooth, maintain debris away from the cutting face of the device and to reduce instrument failure.

The relative size of the cutting surface(s) versus the non-contact surface(s) can be varied as desired. Some variations between the cutting surface and non-contact surface can vary in size, including but not limited to about a 1:1, 2:1, or 4:1 ratio. These ratios can be of a length of the generally circular cutting surface(s) of the non-circular circumference to a length of the linear non-contact surfaces of the non-circular circumference. The angle and direction in which the non-contact surface helically extends along the cutting length can be varied as desired. That is, the non-contact surface can complete one revolution around the instrument in 20 mm, and in another embodiment the non-contact surface can complete one revolution around the instrument in 30 mm. The length of the instrument may vary. In one embodiment, the length of the instrument can range from 5 mm to 80 mm. In other embodiments, the length can range from 5 mm to 60 mm, from 5 mm to 50 mm, and from 15 mm to 40 mm. In one embodiment, the length of the instrument is 25 mm, and in another the length is 40 mm. The diameter of the instrument may also vary. In one embodiment, the diameter of the instrument can range from 0.02 mm to 8.0 mm. In other embodiments, the diameter can range from 0.02 mm to 6.0 mm, from 0.02 mm to 4.0 mm, and from 0.05 mm to 3.0 mm. In one embodiment, the instrument may taper in a parallel or symmetrical fashion from such that the outer diameter decreases in value along the taper by an amount equal to 0.02 mm to 1.0 mm. For example, for every millimeter of length of the instrument, the taper can increase by 0.02 mm. The taper can alternately be variable such that different segments along the length of the instrument taper at different angles. The cutting surface and/or non-contact surface may include a "right handed" helical twist or "left handed" helical twist.

The endodontic instrument can be used manually or by a powered device. By extending the non-contact surface in a helical pattern, the endodontic instrument will engage the entire area of the canal wall when used in an up-down pecking or reciprocating motion. In one embodiment, the instrument may be used with a "hand piece" in rotation or reciprocation or manually. A method of using one of the above-described endodontic instruments can include inserting the cutting portion of the instrument at least partially into a root canal, and reciprocating the instrument along the axis of the cutting portion to remove dentin. The method may further include rotating the instrument about the axis of the cutting portion.

The instrument is designed to engage the tooth structure at every point along its entire length ensuring both cutting and removal of debris simultaneously. Additionally, the instrument is less likely to fracture during use due to the even distribution of torsional forces along the length of the instrument.

The instrument may be composed of metal, including but not limited to stainless steel, nickel titanium, inconel, ceramic, carbide, metal alloys of iron, nickel, titanium, tungsten, copper, niobium, hafnium, aluminum, brass, bronze, galvanized steel, high carbon steel, and alloys and combinations of these materials. The instrument may also be composed of plastic, resin, and/or ceramic.

A kit can be provided that includes two or more endodontic instruments as described above, each having a different size or shape. This can provide a user with multiple options of instruments during a related procedure.

Various embodiments, including those in accordance with the present invention, were subject to computer-simulated solid-model testing. The following three endodontic instruments were tested.

A First Conventional Design of a standard conventional reamer does not have a non-contact surface. Instead, it is a completely round instrument (360 degrees) that only contains cutting flutes. The First Conventional Design has more mass than the other two designs described below because it does not contain a grounded flat, i.e. a non-contact surface. The First Conventional Design has a tapered shaft that has been twisted sixteen turns to form flutes at the tip of the shaft.

A Second Conventional Design is the reamer or instrument shown in FIG. 1, and has a tapered shaft that has been twisted sixteen turns to form flutes at the tip of the shaft. The Second Conventional Design includes a tapered flat, i.e. a non-contact surface, that is not helical and that extends the length of the flutes.

Figure 2A:
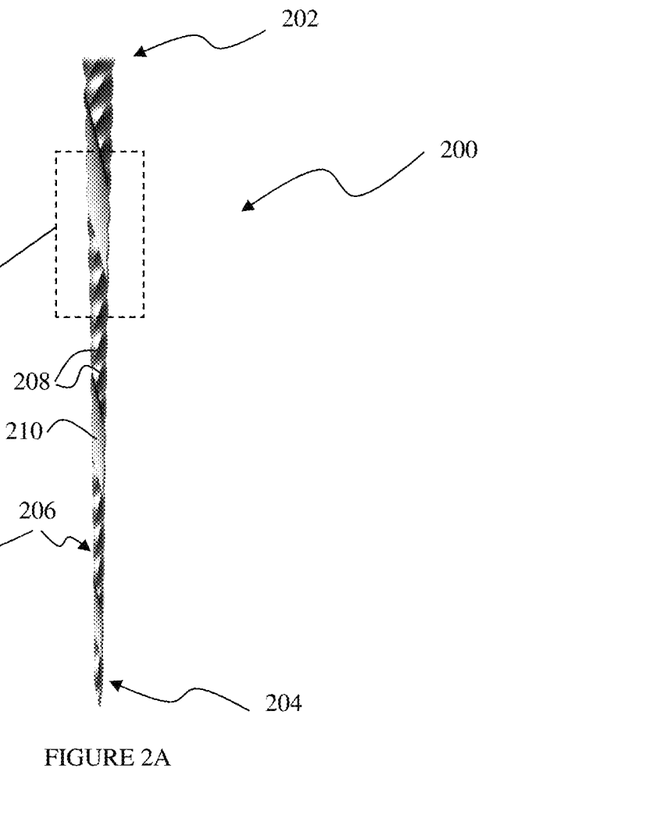
FIGS. 2A and 2B are perspective views of an endodontic instrument having a cutting surface and a non-contact surface helically extending along the length of the instrument according to one embodiment of the present invention.
Figure 2B:
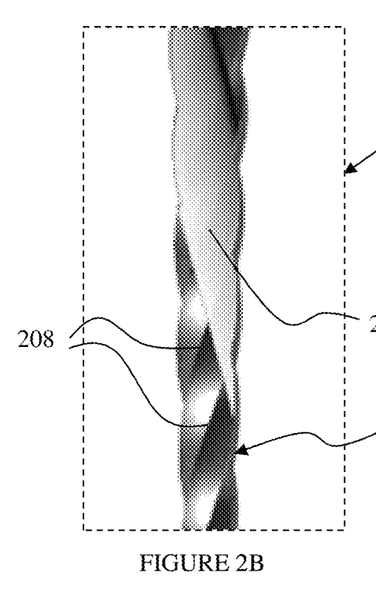
Figure 3A:
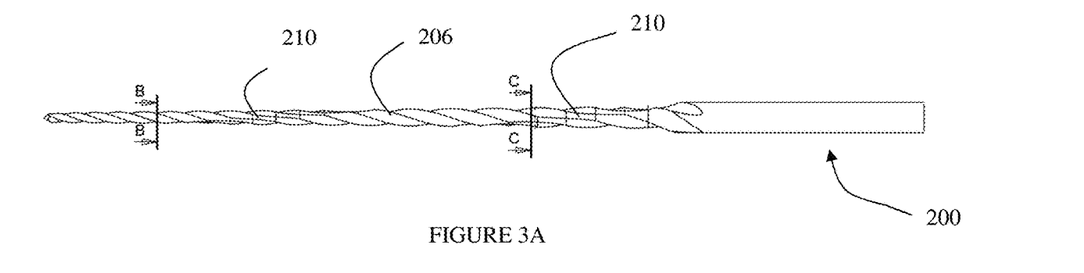
FIG. 3A is a plan view of the instrument shown in FIGS. 2A and 2B.
Figure 3B:
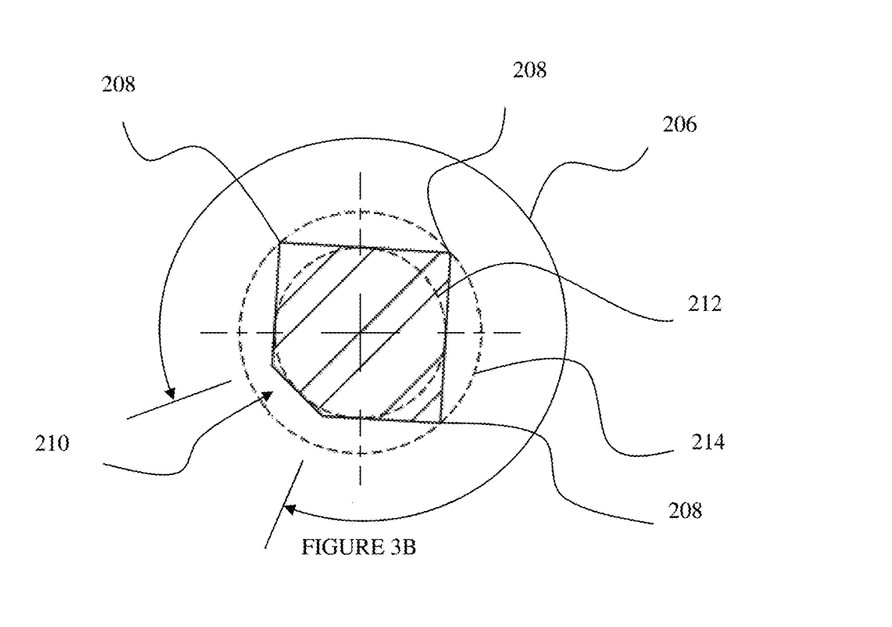
FIGS. 3B and 3C are sectional views taken along the lines B-B and C-C, respectively, of FIG. 3A.
Figure 3C:
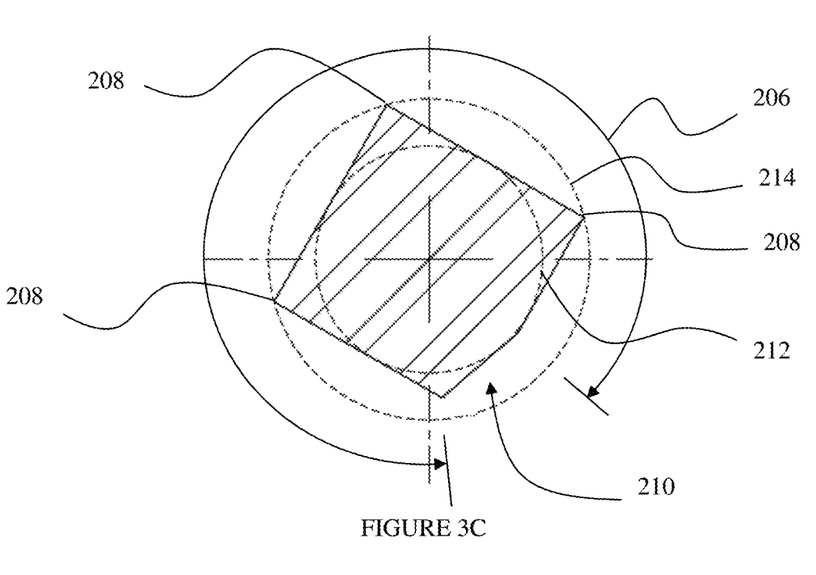

The Novel Design is as shown in FIG. 2A and includes the new improved design with the helical flat, i.e. a non-contact surface extending helically in the first direction along the length of the instrument. The Novel Design has a tapered shaft that has been twisted sixteen turns to form flutes at the tip of the shaft, with a helical tapered flat ground the length of the flutes in the opposite direction of the flutes.

The first study performed was a design study, in which two static studies and two fatigue studies were run on all three designs. In each case, the instrument was fixed by its handle and a uniform load was applied to the flute zone of the shaft. A load of 25 g (0.055 lbs) was loaded on each design until failure. The factor of safety is based on a maximum load (45 g or 0.1 lbs) on the instrument while in constant operation at its "yield" or breaking point. A safety factor less than one indicates a less than "safe" condition.

Figure 8:
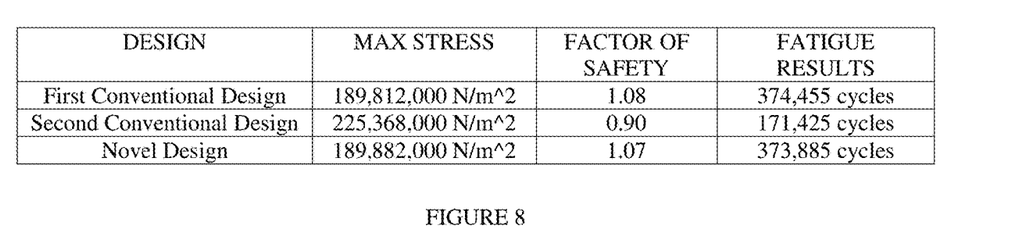
FIG. 8 is a chart showing the results of a design study.

The results of the testing are presented in FIG. 8. The Novel Design performed similarly to The First Conventional Design, though the Novel Design endured a greater maximum stress as compared with the First Conventional Design. This is because of the helical non-contact surface or ground flat cut in the opposite direction of the spiral flutes. The Second Conventional Design is about half the strength of the other two designs, which is likely due to the non-helical tapered flat that extends the length of the flutes. This flat removes half of the material away from the shaft weakening the shaft, in comparison with the other tested designs.

The second study performed was a torsion study, in which a static torsion study was run on all three designs. In each case, the instrument was fixed by the hole in its handle and a torque load was applied to the flute zone at the end of the shaft. A torque load of 0.00625 lb-in (0.1 oz-in) was used as a load on the flute zone until failure. This study was run to show the instruments at a failure state to compare which design is the strongest torsionally.

Figure 9:
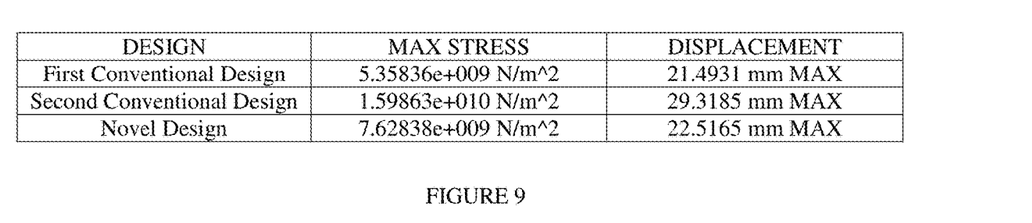
FIG. 9 is a chart showing the results of a torsion study.

The results of the testing are presented in FIG. 9. The Novel Design performed similarly to The First Conventional Design, though the Novel Design has more displacement and endured a greater maximum stress as compared with the First Conventional Design. This is because of the helical non-contact surface or ground flat cut in the opposite direction of the spiral flutes. Again, the Second Conventional Design is about half the strength of the other two designs, which is likely due to the non-helical tapered flat that extends the length of the flutes.

In the design study, the loads were applied to the cutting edge of each tool design to simulate the cutting force applied at the cutting edge of the tool. In the torsion study, the loads were applied to the cutting edge of each tool design to simulate the torque of the cutting force applied at the cutting edge of the tool. Both studies showed the following. With the Second Conventional Design, a much higher stress level is seen than with the other two because the cutting edge runs the full length of the flute without relief along the cutting edge. The Novel Design has a higher stress level than the First Conventional Design because it has a cutting edge and the First Conventional Design does not have a cutting edge. The Novel Design has a much lower stress level than the Second Conventional Design because the cutting edge on the Novel Design is helical so there are reliefs along the edge of the cutting surface reducing the effective tangential force applied normal to the spiral flutes.

Based on the findings of these studies, the Novel Design is the best tool of the three designs for cutting. Because the Novel Design has a helical cutting edge it cuts more efficiently, pulling cutting debris out of the hole as it cuts. The First Conventional Design has no additional cutting edge, and is therefore not as efficient.

Due to its helical geometry, the Novel Design has been proven to exhibit superior performance as compared to the First and Second Conventional Designs in terms of cutting efficiency, torsional strength, flexural strength, and debris removal. Additionally, the Novel Design proved to be at least as strong as the First Conventional Design despite having less mass. The First Conventional Design has more mass than the other two designs because it does not contain a grounded flat. The simulation showed that because of the unique and non-obvious geometry of the Novel Design, it was at least as strong as the First Conventional Design while outperforming the latter in terms of cutting efficiency, tooth engagement, and debris removal. This is because the forces are evenly distributed along the length of the instrument in the Novel Design. The Novel Design also surpassed the Second Conventional Design in terms of durability (less breakage), cutting efficiency, and debris removal because the cutting edges engage the tooth structure in 360 degrees as well as up and down. Thus, the introduction of a helical "flat" or non-contact surface along the length of the instrument (as in instruments 200 and 300) is a very significant improvement which was not obvious by any means as shown by the computer simulation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:
1. An endodontic instrument comprising:
a cutting portion having upper and lower ends spaced apart along an axis, a cutting surface extending helically along the axis, and a non-contact surface extending helically along the axis,
wherein a cross section of the cutting portion in a plane perpendicular to the axis has a non-circular circumference, and
wherein the cutting surface extends about a first portion of the non-circular circumference, and the non-contact surface forms a linear segment that extends about a second portion of the non-circular circumference,
wherein the cutting surface includes cutting blades that extend helically along the cutting surface,
wherein the cutting surface and the non-contact surface extend helically along the axis from the upper end to the lower end in a first rotational direction, and the cutting blades extend helically along the cutting surface and helically along the axis from the upper end to the lower end in a second rotational direction that is opposite from the first rotational direction,
wherein every cross section of the cutting portion along the axis in a plane perpendicular to the axis has a linear segment formed by the non-contact surface, such that the non-contact surface formed by the linear segments extends continuously and uninterrupted along the entire cutting portion, and wherein the endodontic instrument is configured to be inserted into a root canal of a tooth and rotated, to cut and shape the root canal and remove debris therefrom, and is configured to provide reduced stress to the tooth and the endodontic instrument in use.

2. The instrument of claim 1, wherein every cross section of the cutting portion along the axis in a plane perpendicular to the axis has a non-circular circumference.

3. The instrument of claim 1, wherein the cutting portion further includes a second cutting surface extending helically along the axis, and a second non-contact surface extending helically along the axis, wherein the non-circular circumference includes a third portion about which the second cutting surface extends and a fourth portion about which the second non-contact surface extends and forms a second linear segment of the circumference.

4. The instrument of claim 1, wherein the cutting portion is comprised of metal.

5. The instrument of claim 1, wherein the ratio of a length of the first portion of the non-circular circumference to a length of the second portion of the non-circular circumference is 4:1.

6. The instrument of claim 1, wherein a length of the cutting portion is between 5 and 80 mm.

7. The instrument of claim 1, wherein a diameter of the cutting portion is between 0.02 and 8.0 mm.

8. The instrument of claim 1, wherein the cutting portion tapers from the upper end to the lower end so that a diameter of the upper end is between 0.02 and 1.0 mm greater than a diameter of the lower end.

9. A kit comprising:
two or more endodontic instruments according to claim 1 each having a different size or shape.

10. An endodontic instrument comprising:
a cutting portion having upper and lower ends spaced apart along an axis, first and second cutting surfaces extending helically along the axis, and first and second non-contact surfaces extending helically along the axis,
wherein a cross section of the cutting portion in a plane perpendicular to the axis has a non-circular circumference, and
wherein the first cutting surface extends about a first portion of the non-circular circumference, the first non-contact surface forms a linear segment that extends about a second portion of the non-circular circumference, the second cutting surface extends about a third portion of the non-circular circumference, and the second non-contact surface forms a linear segment that extends about a fourth portion of the non-circular circumference,
wherein the first and second cutting surfaces each include cutting blades that extend helically along the first and second cutting surface, respectively,
wherein the first and second cutting surfaces and the first and second non-contact surfaces each extend helically along the axis from the upper end to the lower end in a first rotational direction, and the cutting blades of the first and second cutting surfaces extend helically along the first and second cutting surfaces, respectively, and helically along the axis from the upper end to the lower end in a second rotational direction that is opposite from the first rotational direction,
wherein every cross section of the cutting portion along the axis in a plane perpendicular to the axis has two linear segments formed by the non-contact surfaces, such that the non-contact surfaces formed by the linear segments extend continuously and uninterrupted along the entire cutting portion, and
wherein the endodontic instrument is configured to be inserted into a root canal of a tooth and rotated, to cut and shape the root canal and remove debris therefrom, and is configured to provide reduced stress to the tooth and the endodontic instrument in use.

11. The instrument of claim 10, wherein the first and third portions of the circumference oppose one another.

12. The instrument of claim 10, wherein the second and fourth portions having the first and second linear segments, respectively, are positioned between the first and third portions of the circumference.

13. The instrument of claim 1, wherein the cutting portion is comprised of nickel titanium.

14. The instrument of claim 10, wherein the cutting portion is comprised of nickel titanium.

* * * * *